United States Patent
Davantes et al.

(10) Patent No.: US 6,252,924 B1
(45) Date of Patent: Jun. 26, 2001

(54) METHOD AND APPARATUS FOR MOTION-FREE CARDIAC CT IMAGING

(75) Inventors: Esmeraldo R. Davantes, Pewaukee; Mark E. Woodford, Waukesha, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/409,465

(22) Filed: Sep. 30, 1999

(51) Int. Cl.⁷ .................................................. A61B 6/03
(52) U.S. Cl. ............................................. 378/8; 378/901
(58) Field of Search .................................... 378/4, 8, 901

(56) References Cited

U.S. PATENT DOCUMENTS 4,868,747  9/1989  Mori et al. ............................ 378/901
5,586,201  12/1996  Whiting et al. ........................ 378/8

*Primary Examiner*—Robert H. Kim
*Assistant Examiner*—Drew A. Dunn
(74) *Attorney, Agent, or Firm*—Armstrong Teasdale LLP; Christian G. Cabou

(57) ABSTRACT

A method and apparatus for generating CT images of a moving body part using a CT imaging system. The method includes steps of: scanning a portion of a patient's body including the moving body part utilizing the CT imaging system; collecting image data representative of a sequence of images of the scanned portion of the patient's body; selecting a fixed reference point in images represented by the image data; and selecting at least one image from the sequence of images according to a function of relative positions of the moving body part and the fixed reference point in the sequence of images. A CT scanner or a workstation is configured as an apparatus to implement the method.

22 Claims, 4 Drawing Sheets

METHOD AND APPARATUS FOR MOTION-FREE CARDIAC CT IMAGING

BACKGROUND OF THE INVENTION

This invention relates generally to methods and apparatus for computerized tomographic imaging, and more particularly to methods and apparatus for retrospectively generating computerized tomographic (CT) images of a moving body part without gating signals.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

For some diagnostic procedures, it is necessary to obtain CT images of a moving body part. For example, cardiac calcification scoring requires CT images of the heart without motion-induced artifacts. One known technique for acquiring CT without motion-induced artifacts is to generate x-rays with a scanning electron beam. The scanning electron beam strikes a metal surface and produces a directed beam of x-rays. The beam of x-rays scan a patient's body so rapidly that motion-induced artifacts resulting from motion during a cardiac cycle are avoided. However, electron beam CT imaging systems are more expensive than CT imaging systems having rotating gantries and are not widely available in all hospitals.

Another known technique for acquiring CT images of a heart is to use EKG gating to select times when a best image of the heart is available. An EKG machine is connected to a patient. A cardiac cycle period is determined, for example, as a time between R-peaks of the EKG. Using an R-peak as a reference and the determined cardiac cycle period, image acquisition during a scan is gated so that image data is acquired only during periods of a cardiac cycle for which the heart is nearly stationary. A disadvantage of this technique is that it requires electronic communication between the CT imaging apparatus and the EKG machine. Furthermore, gating times must be estimated in advance. Unfamiliar surroundings and equipment observed by a patient during a CT scan can induce stress in a patient, resulting in variations of a cardiac cycle during a test. Other anomalies, such as preventricular contractions, may also interrupt a steady cardiac cycle. All of these irregularities reduce the accuracy of the estimated gating times, and can result in unacceptable motion-induced artifacts in the acquired images.

It would therefore be desirable to provide methods and apparatus to reduce or eliminate motion-induced artifacts without requiring expensive equipment, such as an electron-beam CT imaging system, or additional gating signals.

BRIEF SUMMARY OF THE INVENTION

There is therefore provided, in one embodiment of the present invention, a method for generating CT images of a moving body part using a CT imaging system, the method including steps of: scanning a portion of a patient's body including the moving body part utilizing the CT imaging system; collecting image data representative of a sequence of images of the scanned portion of the patient's body; selecting a fixed reference point in images represented by the image data; and selecting at least one image from the sequence of images according to a function of relative positions of the moving body part and the fixed reference point in the sequence of images.

Images selected in the above described embodiment of the present invention can be produced by a CT scanning device having an x-ray source on a rotating gantry, without requiring electron-beam radiation techniques. Nevertheless, images produced using method embodiments of the present invention have reduced motion-induced artifacts compared to images obtained by conventional methods. Furthermore, no EKG need be taken at all when the moving body part is a heart, because no gating signals are required for acquisition or subsequent examination and selection of images. Thus, the method is particularly advantageous for obtaining images for calcification scoring diagnostic procedures.

DETAILED DESCRIPTION OF THE INVENTION

Figure 1:
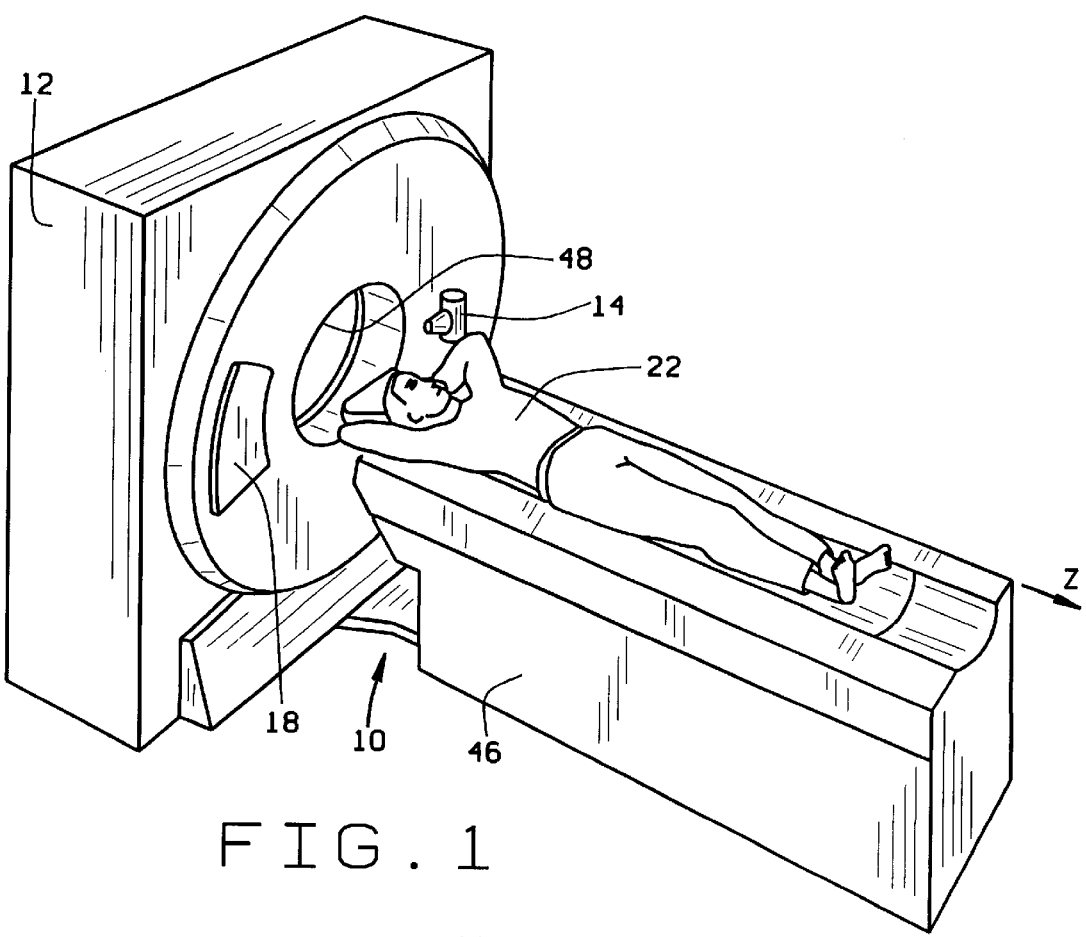
FIG. 1 is a pictorial view of CT imaging system.
Figure 2:
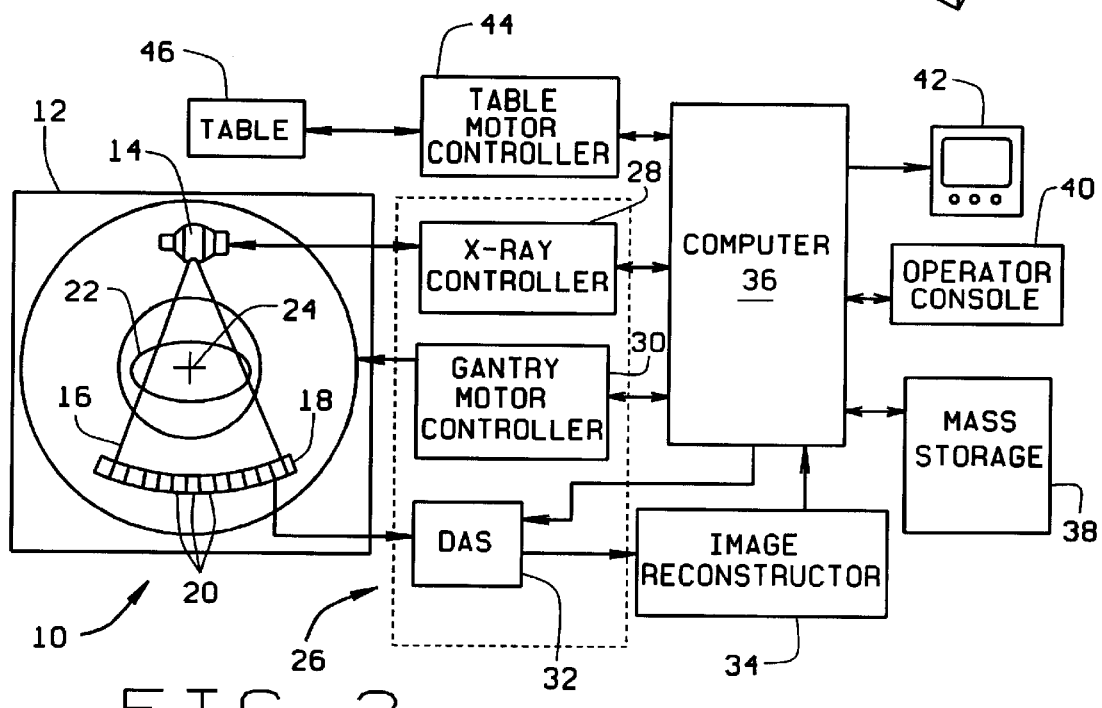
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48 in a direction along a z-axis.

Figure 3:
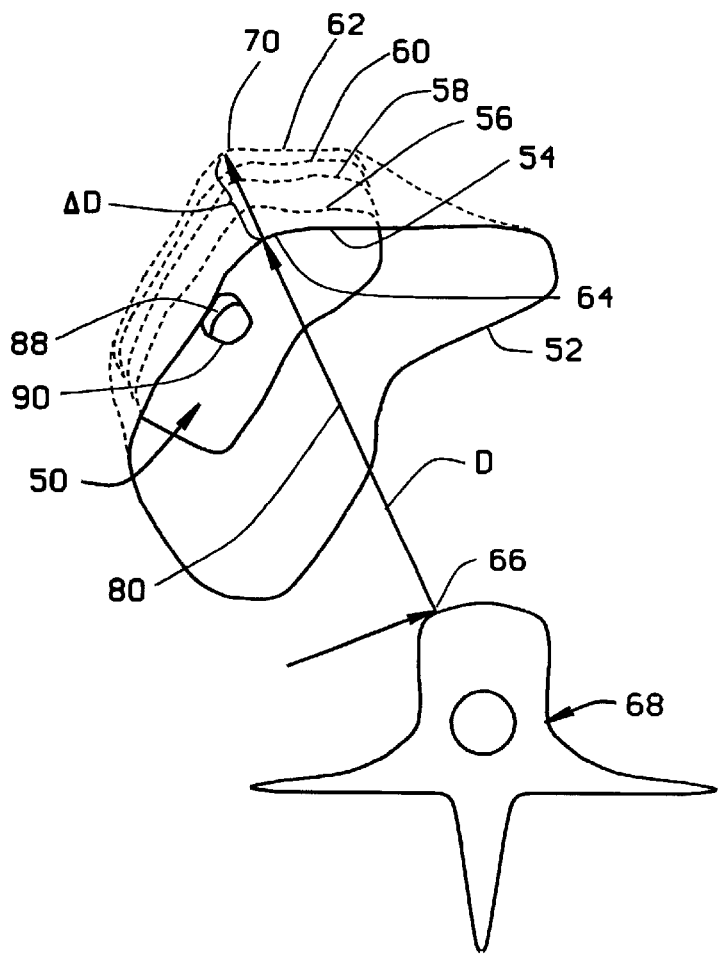
FIG. 3 is a drawing representing a composite of a sequence of scanned image slices, with differences between successive slices shown by dashed lines.
Figure 4:
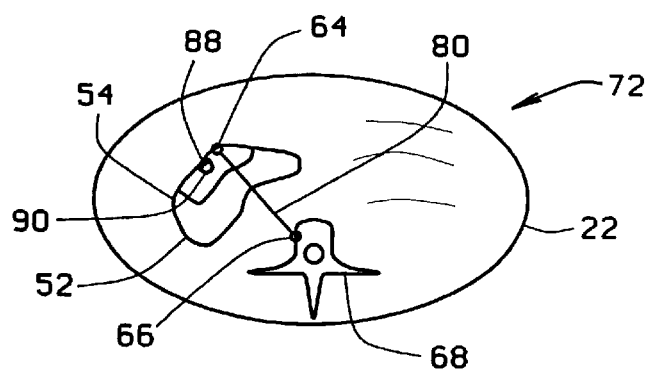
FIGS. 4, 5, 6, and 7 are drawings representing separate images of some of the sequence of scanned image slices represented in FIG. 3.
Figure 5:
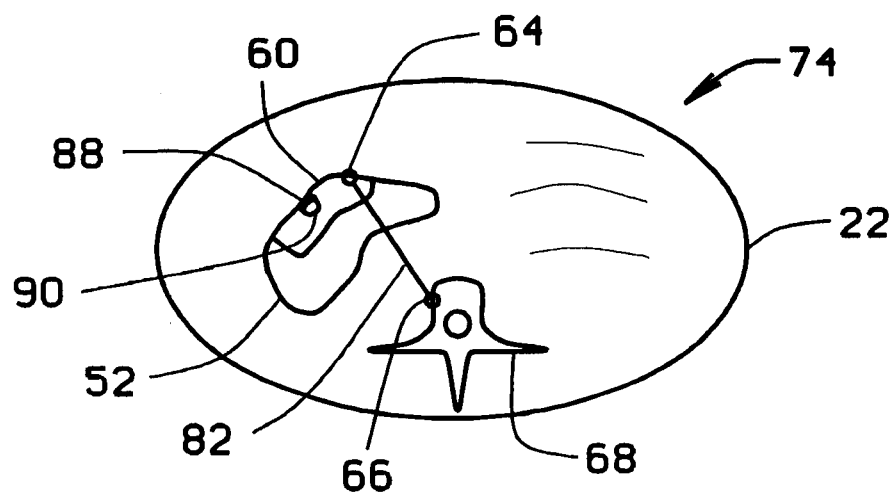
Figure 6:
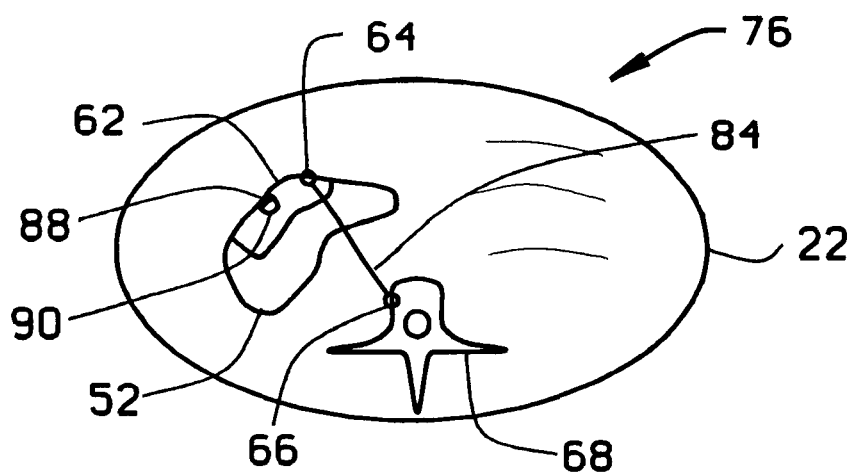
Figure 7:
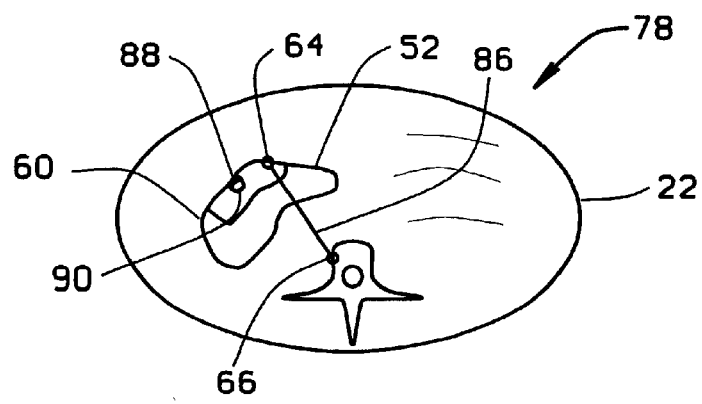

Referring to FIG. 3, in a course of a single cardiac cycle, a ventricular chamber 50 of heart 52 of patient 22 is primarily responsible for expelling oxygenated blood throughout his or her body. The expansion phase of this cycle is known as the diastolic phase. The contraction phase is known as the systolic phase. A ventricular wall 54 of heart 52 will expand 56, 58, 60, 62 as its chamber 50 fills with oxygenated blood received from pulmonary veins. (Reference numerals 54, 56, 58, 60, and 62 are used to indicate the ventricular wall in various different stages of the cardiac cycle.) This oxygenated blood is routed through the left atrium into left ventricle 50. Ventricular walls 54 expand until a voltage potential threshold is exceeded. This electrical event precedes mechanical contraction 62, 60, 58, 56, 54 of left ventricle 50. As left ventricle 50 contracts, oxygenated blood passes through the aortic valve into the aorta.

In one embodiment, using a cine scan, CT imaging system 10 tracks and measures an area of ventricular wall 54 relative to a fixed reference point 66, for example, a point 66 on spine 68 of patient 22. As ventricular chamber 50 fills with blood, ventricular wall 54 begins to expand 56, 58, 60, 62. A distance D between spine 68 and point 64 on ventricular myocardial wall 54 increases 56, 58, 60, 62, as revealed in consecutive CT cine images. This distance continually and gradually increases until the aforementioned threshold potential is reached 70.

At or about this point in the electromechanical phase of the cardiac cycle, little, if any, increases in measured distance D+ΔD occur. Heart 52 is at a moment prior to systole, its relatively quietest moment in the cardiac cycle. As heart 52 enters its systolic phase, left ventricular wall 62 contracts to expel blood. A marked change in a spinal-myocardial measured distance D+ΔD to D is observed. This distance drastically changes and diminishes during the systolic phase of the heart.

In one embodiment, and referring to FIGS. 4, 5, 6, and 7, images are selected in which little, if any, changes in observed spinal-myocardial measured distance is observed to obtain motion artifact-free images. Although a steady heart rate is desirable, it is not necessary during image acquisition. A CT imaging system 10, for example, system 10 of FIGS. 1 and 2 or a four-slice imaging system, is used to scan a portion of heart 52 of patient 22. Cine scanning is used so that imaging is performed continuously for a selected period of time without moving table 46. Each cine scan is made sufficiently long to ensure that a complete cardiac cycle of heart 52 is included. For example, in an approximately two second cine scan, image data representative of a sequence of approximately 44 images are obtained. Each image is approximately 0.1 second apart from the next. These 44 images include at least one complete cardiac cycle. Additional two-second cine scans are taken as needed. Table 46 is stepped between each two-second cine scan so that image slices from a subsequent scan do not overlap a volume imaged in slices from previous scans. In one embodiment, table 46 is stepped an amount equal to a total thickness of the image slices acquired, to obtain a set of slices adjacent to, but not overlapping, slices obtained prior to each step.

A user, such as a surgeon or physician, retrospectively reviews images obtained during the cine scan. For example, images 72, 74, 76, and 78 of FIGS. 4, 5, 6, and 7 represent part of a sequence of image data, in an order in which the image data is acquired. A fixed feature of the images is determined, for example, point 66 on spine 68 of patient 22. Point 66 is used as a fixed reference point. A line 80 is extended from point 66 towards a reference point 64 on left ventricular wall 54 in a first image of the sequence of images. For example, a superimposed line 80 is drawn on a display screen displaying image 72. In a second, subsequently obtained image 74, a line 82 is extended from the same fixed point 66 on spine 68 to the same reference point 64 on the left ventricular wall, which is now at 60. It is then determined whether the length of line 82 has increased or decreased relative to line 80 in image 72. If heart 52 happens to have been caught in one phase of its cardiac cycle, for example, the length increases. Lines 84 and 86 are drawn on subsequent images 76, 78 until the length a line, for example, line 86, just begins to decrease or remain constant relative to a line, for example, line 84, drawn on a previous image. Let us assume that the image at which this occurs (image 78 of FIG. 7 in this example) is the ith image in a sequence of 44 images.

The ith image 78 provides a satisfactory image with reduced motion-induced artifacts from which to measure calcification 88 of pulmonary arteries 90. In one embodiment, a plurality of images are used for cardiac calcification scoring. These images are the ith image 78, and a selected number of images in sequence. For example, images are used back to a final image 76 at which line 84 between point 66 on spine 68 and point 64 on left ventricular wall 62 is still slightly increasing.

Depending upon in which image this occurs, the i-1th image 76 and possibly the i-2nd image 74 are scored in conjunction with the ith image 78. In this embodiment, therefore, the selected number of images of the sequence is no greater than two. In another embodiment, only one of images 78, 76, and 74 is used for calcification scoring when it is determined that a single image is adequate for such use. This image, e.g., image 76, is one in which little, if any, change in line length 84 is observed relative to adjacent images 74, 78.

The lengths of lines 80, 82, 84, 86 represent distances between reference points 64 and 66. In another embodiment, images are selected as a function of a change in the sign of line length changes between consecutive images, or when the change becomes zero.

When multiple slices of image data are acquired simultaneously, it will be understood that a method embodiment of the present invention generally need not necessarily be repeated for each sequence of parallel slices. Instead, all images of parallel slices taken at the same time as those selected for one of the parallel slices will generally be equally satisfactory.

Because known CT imaging system 10 provide gantry 12 rotation speeds that are a substantial fraction of a cardiac cycle, each of the images in both cine scan and segmented helical scan embodiments are reconstructed from less that a full 360° view angle of data. These views are known as segmented images, and the data representing them is known as segmented image data. For this reason, in one embodiment, imaging system 10 is said to collect segmented image data. Because segmented image data is collected in a relatively short time for each image, motion-induced image artifacts are reduced relative to images reconstructed from longer, full scans. However, embodiments having gantry 12 rotation speeds sufficiently fast to permit reconstruction of views from a full 360° view angle with reduced image artifacts are possible.

In addition to the usual scanning and data acquisition functions of CT imaging system 10 of FIGS. 1 and 2, in one embodiment, computer 36 is programmed to display successive images, for example, images 72, 74, 76, 78 of FIGS. 4, 5, 6, and 7, on display 42. Lines and successive images are manipulated via console 40 or another suitable input device or devices. Computer 36 is also programmed to calculate and display line lengths drawn by an operator on images displayed on display 42.

Figure 8:
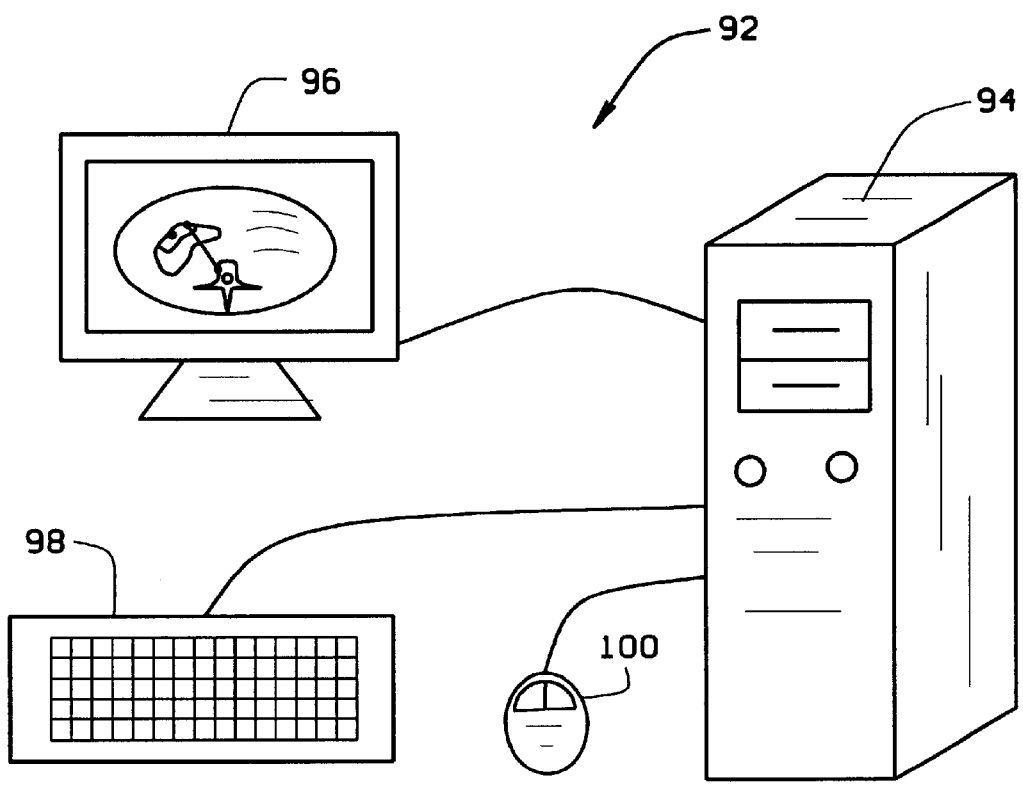
FIG. 8 is a pictorial drawing of an embodiment of a workstation of the present invention.

In another embodiment, image data acquired by CT imaging system 10 is downloaded or transferred to a separate workstation 92, shown in FIG. 8. Any of various transfer modes, for example, data transfer via recorded media or network communication, are suitable. Workstation 92 includes, in one embodiment, a system unit 94 having a processor and memory, a display 96, and one or more operator input devices such as a keyboard 98 and a mouse 100. The processor is programmed to display and manipulate images on display 96 and to calculate and display line lengths drawn on the screen by an operator using input devices 98 and 100.

From the preceding description of various embodiments of the present invention, it is evident that motion-induced artifacts of heart images are reduced without requiring expensive equipment, such as an electron-beam CT imaging system, or additional gating signals. Moreover, the added cost of an EKG is avoided in embodiments using cine protocols, because no EKG is required for gating or selection of images.

Although particular embodiments of the invention have been described and illustrated in detail, it is to be clearly understood that the same is intended by way of illustration and example only and is not to be taken by way of limitation. For example, although cardiac imaging embodiments are described in detail above, the invention has more general applicability. Other embodiments applicable to imaging different cyclically moving body parts, such as lungs, will be apparent from reading this specification to those skilled in the art. Also, image recognition techniques can be applied to identify image features. For example, image recognition software can be used either to identify of a pair of reference points for measurement of relative motion or, once reference points are first identified, to identify corresponding reference points on other images. Distances between the automatically identified points can then be easily computed by a central processing unit or microprocessor, and images can be selected by software, based upon selected criteria. The selected criteria may be based upon the line length criteria discussed in conjunction with the manual embodiments can be used, or another criteria selected to optimize a medical application or diagnostic procedure. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for generating CT images of a moving body part using a CT imaging system, said method comprising the steps of:

scanning a portion of a patient's body including the moving body part utilizing the CT imaging system;

collecting image data representative of a sequence of images of the scanned portion of the patient's body;

selecting a fixed reference point in images represented by the image data; and selecting at least one image from the sequence of images according to a function of relative positions of the moving body part and the fixed reference point in the sequence of images.

2. A method in accordance with claim 1 wherein collecting image data representative of a sequence of images of the scanned portion of the patient's body comprises the step of collecting segmented image data.

3. A method in accordance with claim 2 wherein scanning a portion of a patient's body comprises the step of cine scanning the portion of the patient's body.

4. A method in accordance with claim 3 further comprising the steps of selecting a reference point on the moving body part, and identifying the reference point on the moving body part in each of the sequence of images of the scanned portion of the patient's body, and wherein selecting at least one image from the sequence of images as a function of relative positions of the moving body part and the fixed reference point in the sequence of images comprises comparing distances between the reference point on the moving body part and the fixed reference point in the sequence of images and selecting the at least one image as a function of distance changes between consecutive images of the sequence of images.

5. A method in accordance with claim 4 wherein selecting the at least one image comprises selecting at least one image of the sequence of images within a selected number of images of an image in which a change in the distances reverses its sign or becomes constant.

6. A method in accordance with claim 5 wherein the selected number of images is no greater than two.

7. A method in accordance with claim 6 wherein scanning a portion of a patient's body comprises the step of scanning a portion of the patient's body including a heart and a spine, the moving body part is the heart and the selected fixed reference point is a point on the spine.

8. A method in accordance with claim 4 wherein at least one of said steps of selecting a fixed reference point in images represented by the image data, of selecting at least one image from the sequence of images based upon relative positions of the moving body part and the fixed reference point in the sequence of images, of selecting a reference point on the moving body part, and of identifying the reference point on the moving body part in each image of the sequence of images of the scanned portion of the patient's body, is performed by a processor utilizing image recognition software.

9. A method in accordance with claim 1 wherein at least one of said steps of selecting a fixed reference point in images represented by the image data and of selecting at least one image from the sequence of images based upon relative positions of the moving body part and the fixed reference point in the sequence of images is performed by a processor utilizing image recognition software.

10. A method in accordance with claim 1 wherein scanning a portion of a patient's body comprises the step of scanning a portion of the patient's body including a heart and a spine, the moving body part is the heart and the selected fixed reference point is a point on the spine.

11. A CT imaging system for generating CT images of a moving body part, said system configured to:
   scan a portion of a patient's body including the moving body part;
   collect image data representative of a sequence of images of the scanned portion of the patient's body;
   select a fixed reference point in images represented by the image data; and
   select at least one image from the sequence of images according to a function of relative positions of the moving body part and the fixed reference point in the sequence of images.

12. A system in accordance with claim 11 wherein said system being configured to collect image data representative of a sequence of images of the scanned portion of the patient's body comprises said system being configured to collect segmented image data.

13. A system in accordance with claim 12 wherein said system being configured to scan a portion of a patient's body comprises said system being configured to cine scan the portion of the patient's body.

14. A system in accordance with claim 13 further configured to select a reference point on the moving body part, and to identify the reference point on the moving body part in each of the sequence of images of the scanned portion of the patient's body,
   and wherein said system being configured to select at least one image from the sequence of images as a function of relative positions of the moving body part and the fixed reference point in the sequence of images comprises said system being configured to compare distances between the reference point on the moving body part and the fixed reference point in the sequence of images and to select the at least one image as a function of distance changes between consecutive images of the sequence of images.

15. A system in accordance with claim 14 wherein said system being configured to select the at least one image comprises said system being configured to select at least one image of the sequence of images within a selected number of images of an image in which a change in the distances reverses its sign or becomes constant.

16. A system in accordance with claim 15 wherein the selected number of images is no greater than two.

17. A system in accordance with claim 16 wherein said system being configured to scan a portion of a patient's body comprises said system being configured to scan a portion of the patient's body including a heart and a spine, and wherein the moving body part is the heart and the selected fixed reference point is a point on the spine.

18. A system in accordance with claim 11 wherein said system configured to scan a portion of a patient's body comprises said system being configured to scan a portion of the patient's body including a heart and a spine, and wherein the moving body part is the heart and the selected fixed reference point is a point on the spine.

19. A workstation for selecting CT images of a moving body part obtained from image data representing a sequence of images acquired by a CT imaging system, said workstation comprising a system unit, at least one operator input device, and a display, wherein said system unit is configured to:
   select a fixed reference point in images represented by the image data; and
   select at least one image from the sequence of images as a function of relative positions of the moving body part and the fixed reference point in the sequence of images.

20. A workstation in accordance with claim 19 further configured to select a reference point on the moving body part, and to identify the reference point in each of the sequence of images of the scanned portion of the patient's body, and wherein said workstation being configured to select at least one image from the sequence of images as a function of relative positions of the moving body part and the fixed reference point in the sequence of images comprises said workstation being configured to compare distances between the reference point on the moving body part and the fixed reference point in the sequence of images and to select the at least one image as a function of distance changes between consecutive images of the sequence of images.

21. A workstation in accordance with claim 20 wherein said workstation being configured to select the at least one image comprises said workstation being configured to select at least one image of the sequence of images within a selected number of images of an image in which a change in the distances reverses sign or becomes constant.

22. A workstation in accordance with claim 21 wherein the selected number of images is no greater than 2.

* * * * *